United States Patent [19]

Theurer et al.

[11] 4,040,292
[45] Aug. 9, 1977

[54] METHOD AND APPARATUS FOR INDICATING THE DENSITY OF BALLAST

[75] Inventors: Josef Theurer, Vienna, Austria; Waldemar Friedrich Thöle, Johannesburg, South Africa

[73] Assignee: Franz Plasser Bahnbaumaschinen-Industriegesellschaft m.b.H., Vienna, Austria

[21] Appl. No.: 644,325

[22] Filed: Dec. 24, 1975

[30] Foreign Application Priority Data

Jan. 28, 1975  Austria ................................ 617/75

[51] Int. Cl.² ........................ G01N 3/40; G01N 33/24
[52] U.S. Cl. .......................................... 73/84; 104/12
[58] Field of Search ................ 73/78, 81, 83, 84; 104/12

[56] References Cited

U.S. PATENT DOCUMENTS

| | | | |
|---|---|---|---|
| 2,117,985 | 5/1938 | Ridenour | 73/84 |
| 2,833,144 | 5/1958 | Miller et al. | 73/84 |
| 3,096,724 | 7/1963 | Kershaw | 104/12 |
| 3,807,311 | 7/1972 | Plasser et al. | 104/12 |

Primary Examiner—James J. Gill
Attorney, Agent, or Firm—Kurt Kelman

[57] ABSTRACT

A method and apparatus for indicating the density of a mass of course particles, such as track ballast, uses the immersion of a tool capable of penetrating into the mass, for instance a tamping tool. The degree of the density is a function of the time of the immersion stroke, the length of the immersion stroke and the immersion force. One of these parameters is measured while the other two parameters are predetermined to determine the measured value of the degree of density, and the measured value is indicated. In a mobile track tamping machine, this is accomplished by actuating a time measuring device by switching elements arranged to be actuated by the immersing tool for measuring the time required by the tool for immersion in the ballast through a predetermined immersion stroke. The time measuring device transmits corresponding time signals to an indicator.

11 Claims, 2 Drawing Figures

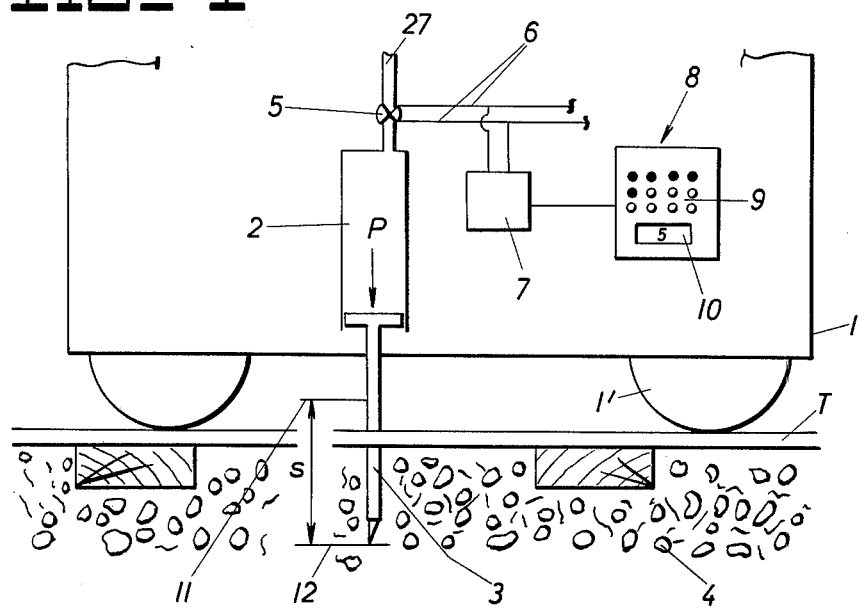
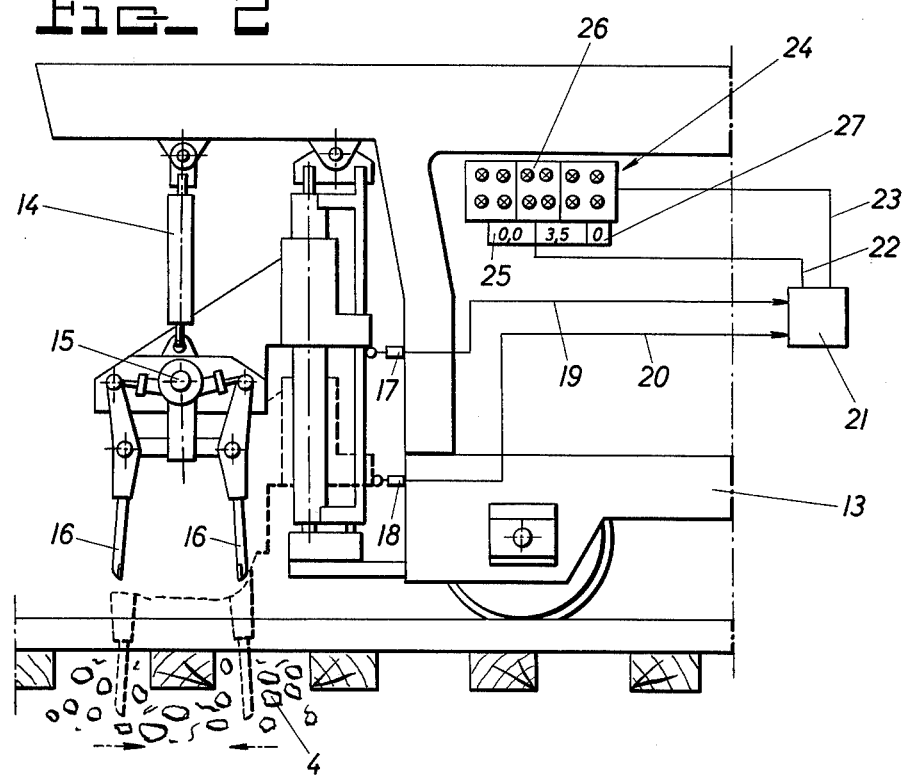

METHOD AND APPARATUS FOR INDICATING THE DENSITY OF BALLAST

The present invention relates to improvements in a method and apparatus for indicating the density of a mass of coarse particles, such as track supporting ballast, by immersing a tool capable of penetrating into the mass in the mass. A preferably hydraulic drive applies a force to the tool to immerse the same in the ballast and the degree of the density is a function of the length of the immersion stroke under a predetermined applied force. The corresponding value may be measured and indicated as well as recorded.

For instance in the case of a track bed, the determination of the condition or density of the ballast in the bed may be of considerable importance because this determination will guide the work required to renew the track bed, i.e. it will be determinative of the required ballast compaction forces during tamping operations. Thus, the degree of prevalent ballast density will determine the degree of force to be applied to the ballast tamping tools in respect of their reciprocation and/or vibration. Therefore, it is essential to know the ballast condition before the track maintenance work starts, i.e. before grading and tamping the track, so that the ballast tamping tools may be most effectively operated.

U.S. Pat. No. 3,807,311, dated Apr. 30, 1974, proposes a mobile track tamping and leveling machine which incorporates a pressure roller whose lowering into the ballast is used to determine and indicate the density of the ballast. The density of the ballast is a function of the immersion depth of the pressure roller. However, since a pressure roller is not shaped to penetrate into the ballast, this apparatus can measure the ballast density only at the surface, thus giving some indication of the overall condition of the ballast bed but being incapable of determining the density of the ballast closer to the subgrade deep within the body of the bed.

It is the primary object of this invention to provide a method and apparatus of the indicated type, which makes it possible to determine and indicate the density of a mass of coarse granular particles, particular of a ballast bed, at any desired zone of the mass deep within the body thereof.

This and other objects are accomplished in accordance with the method of the invention by measuring one of the following three parameters: time of immersion stroke, length of immersion stroke and immersion force of the tool while predetermining the two other parameters to determine a measured value of the degree of density, which is a function of these parameters. The measured value is indicated and, if desired, recorded. The value may be indicated digitally, in analog manner, for instance acoustically, or visually, for instance.

The apparatus of the present invention is combined with, and may be mounted on, a mobile track tamping machine and comprises a tool capable of penetrating into the ballast, a drive for applying a force to the tool to immerse the same in the ballast, a signal emitter producing a signal indicating the density of the ballast, and an indicator associated with the transmitter to receive and indicate the signal. According to this invention, the signal emitter of such an apparatus is a time measuring device for measuring the time required by the tool for immersion in the ballast through a predetermined immersion stroke, and switching elements are arranged to be actuated by the immersing tool and for actuating the signal emitter to transmit corresponding time signals to the indicator.

This method and apparatus make it possible accurately to determine the density of the interior of masses of coarse particles as a function of the resistance encountered by the immersing tool. Thus, the operator of a mobile track tamper, for instance, will be enabled to use appropriate tamping methods dependent on the accurate indication of the ballast bed condition. Thus, before a lengthy track section is tamped, particularly in case of badly encrusted ballast beds, all regions of the bed may be carefully analyzed. If preferred, this analysis may be effectuated simultaneously with the tamping operation. In other words, the invention provides a variety of possibilities, any of the three indicated parameters being measured in relation to the two other predetermined parameters to obtain the desired value.

The machine of this invention is simple in structure and provides highly accurate ballast density measurements. It may readily be built into existing mobile tampers at low cost or the existing tamping tools themselves may be used as the measuring tool.

The above and other objects, advantages and features of the present invention will be more fully understood from the following detailed description of certain now preferred embodiments thereof, taken in conjunction with the accompanying drawing wherein FIG. 1 is a highly schematic side view of one embodiment of an apparatus according to this invention; and FIG. 2 shows another embodiment of the apparatus in combination with a partial side view of a mobile track tamping machine.

Referring now to the drawing and first to FIG. 1, a simple apparatus is illustrated for practicing the method of the invention. This apparatus essentially consists of frame 1 mounted for mobility on track T by means of wheels 1'. A slim tool 3 capable of penetrating into ballast 4 is mounted on the mobile frame, the tool being constituted by the piston rod of hydraulic cylinder-and-piston drive 2 which applies force P to the tool to immerse the same in the ballast. The configuration of the tool is adapted to the average particle size of the ballast to enable the tool to pass through the ballast when force P is applied thereto in a vertical downward direction. Hydraulic fluid is delivered to the cylinder of the drive through conduit 27, a solenoid valve 5 in the conduit controlling the fluid flow and the corresponding force applied to the tool. Electric conductors 6, 6 of a control circuit for operating solenoid valve 5 are connected to time measuring device 7 which thus measures the time required by tool 3 for immersion in ballast 4 through a immersion stroke predetermined by the opening and closing of the solenoid valve. The resultant time signal is transmitted from time measuring device 7 to indicator 8 connected thereto. The illustrated indicator comprises a system of lamps 9 arranged for step-wise actuation of an increasing number of lamps in response to an increasing value in the time signals, and a digital indicator 10 with a scale which numerically indicates this value.

The density of ballast 4 at a predetermined immersion stroke $s$, say $s = 25$ cm, and a predetermined force P applied to tool 3, say $P = 150$ kp, is determined by measuring the time $t$ required for vertically moving tool 3 from upper rest position 11 to lowest position 12 in the ballast, i.e. between the two end positions which delimit the immersion stroke $s$. This time is a direct function of, i.e. it is in direct proportion to, the density of the ballast, i.e. the time signal is an accurate signal of the ballast density. This signal is visually indicated in an analog manner by the serial lighting of successive lamps in display 9 and digitally on scale 10. When solenoid valve 5 is opened to begin the immersion stroke, electrical control circuit 6 will actuate time measuring device 7 and the device will be shut off when tool 3 has reached its lowest position 12, i.e. when the immersion stroke is ended, for instance by a stop or limit switch or the like. As the measured time increases, lamp after lamp on display panel 9 is lit up, five actuated lamps being shown in FIG. 1, to indicate the density of the ballast. Scale 5 will show this condition in numbers, the number 5 being illustrated. Instead of the visual indication by lamps, an acoustical system may be used.

It will be obvious to those skilled in the art that, instead of measuring the time parameter, with the parameters of the length of the immersion stroke and the immersion force of the tool predetermined and known, it would also be possible and lead to the same result to measure the length of the immersion stroke, with the two other parameters predetermined, or similarly to measure the immersion force. The measurement of any one unknown parameter, with the other two parameters known, will solve the equation and give an accurate signal of the ballast density.

FIG. 2 shows mobile track tamping machine 13 on which the apparatus for indicating the density of ballast 4 is mounted. This machine advances along the track in an operating direction during track work. A vertically adjustable tamping unit 15, which may have any conventional design, is mounted on the machine frame and comprises pairs of tamping tools 16 reciprocal in the operating direction, as indicated by a pair of arrows in broken lines. The operation of the vibratory tamping tools for tamping the ballast underneath the track ties is entirely conventional and requires no description. According to the present invention, the tamping tools are used as the tools whose immersion in the ballast is used to measure the ballast density. This assures a particularly dependable and accurate measurement because two tools entering two separate regions of the ballast are used. Furthermore, it is very simple since it does not involve additional tool structures but enables the ballast density to be measured while conventional tamping proceeds. If the ballast tamping plate attached to the lower end of tamping tools 16 has a corrugated or sinuous configuration adapted to the average size of the ballast, as is known in tamping tools, the resistance to immersion of the tools in the ballast will be ideally reduced in a manner assuring most accurate density measurements.

The immersion time $t$ required for the downward movement of the tamping unit from the upper position indicated in full lines to the lower position indicated in broken lines is measured by limit switches 17, 18 in the path of the tamping unit carrier. Electrical conductors 19, 20 connect the limit switches to digital time measuring device 21. When hydraulic cylinder-and-piston drive 14 is operated to lower tamping unit 15 from its upper rest position, the tamping unit carrier will trip switch 17 to send an electric pulse through line 19 to time measuring device 21, thus actuating the device and starting it to count in 0.1 second time units. When the tamping unit has been moved through its immersion stroke to the lowest position, the tamping unit carrier will trip limit switch 18, sending another electric pulse through line 20 to device 21 to shut the same off. A signal corresponding to the counted time units will be transmitted by electrical conductors 22, 23 to indicator 24 arranged in the operating cabin of the machine. The indicator comprises an electronic multiple-lamp system 26 and a scale 25.

The use of a digital time measuring device makes it possible expeditiously and accurately to measure and indicate the elapsed time. Use of the illustrated lamp display systems for visually indicating the measured signals has considerable practical advantages. If desired, a voltage regulator may be interposed between the time signal emitter and the indicator lamps so that, instead of serially lighting up additional lamps, the light intensity may be changed in correspondence to the signal. The use of a light system makes operation in the dark possible.

In system 26, groups of differently colored lights are used, the illustrated display consisting of three groups of lamps, each group having four lamps, for instance of yellow, green and red color. The signal from digital time measuring device 21 is transmitted to system 26 through line 23, respective ones of the differently colored lamps of a group being actuated in accordance with the signal. This will give the operator of the tamping machine a constant visual indication of the ballast density. If too many lamps or groups of lamps are lit up, the operator of machine 13 will know that the ballast is so dense as to require no tamping since the rubble and encrustations in the ballast are such as to make it unsuitable for proper track support.

Digital indicator 25, which receives the signal from transmitter 21 through line 22, gives an added numerical indication of the ballast condition. The indicator comprises two adjacently arranged scales. One of the scales is automatically returned to its zero setting when the tamping unit has been lifted into its rest position. A setting switch 27 enables the other scale to be reset to zero manually. This has the advantage that two successive measurements may be compared to each other. As shown in FIG. 2, measuring value "3.5" is seen on the scale that may be manually reset by switch 27. In the succeeding measurement, the operator of machine 13 may control the tamping pressure of tamping tools 16, 16 on the basis of comparison with this previously read value. In this manner, the density of the tamped ballast will be uniform.

In practicing the method of this invention, it will be advantageous before the actual density measuring operation to make several test measurements in the dirty and encrusted ballast beds as well as in cleaned beds. Such a series of tests will produce a series of comparison values of the three parameters of measurement, and it will then be possible to set the values of these parameters on the basis of the comparison values to obtain a relationship of the three parameters which is suitable for practical operations. This makes it possible to use properly shaped tools and to set the immersion depth and applied force in accordance with practical requirements. During the measuring operation proper, when a ballast bed is to be worked, two of the three parameters are predetermined according to standardized values obtained during the test runs, for instance immersion force P and immersion stroke $s$. The third parameter, in this case immersion time $t$, is then measured by the immersion of the tool 3 or 16 into the ballast, and this measured value is compared with the standardized value resulting from the tests. The degree of density of the ballast is then determined from the ratio of the measured to the standardized value.

Of course, the time of immersion need not be measured digitally and it may be indicated in an analog manner, the time signal being transmitted to a voltage regulator which will change the current intensity in proportion to the signal.

Also, it may be useful not only to build the apparatus of the invention into a mobile track tamper but to combine it therewith by coupling mobile frame 1 to the tamper, either frontwards or rearwards of tamping unit 15. In this manner, the ballast bed density may be accurately analyzed immediately before and/or after the ballast tamping operation.

We claim:

1. In an apparatus for indicating the density of track supporting ballast, combined with a mobile track tamping machine and comprising a tool capable of penetrating into the ballast, a drive for applying a force to the tool to immerse the same in the ballast, a signal emitter producing a signal indicating the density of the ballast, and an indicator associated with the signal emitter to receive and indicate the signal: the improvement of
   1. the signal emitter being a time measuring device for measuring the time required by the tool for immersion in the ballast through a predetermined immersion stroke and
   2. spaced switching elements arranged to be actuated by the displacement of the penetrating tool a predetermined distance and for actuating the signal emitter to transmit corresponding time signals to the indicator.

2. In the apparatus of claim 1, the tool being a ballast tamping tool.

3. In the apparatus of claim 1, the tool being constituted by a ballast tamping unit comprising two reciprocal tamping tools.

4. In the apparatus of claim 1, the track tamping machine comprising a ballast tamping unit and the tool being arranged frontwards of the tamping unit and the direction of advancement of the machine along the track.

5. In the apparatus of claim 1, the track tamping machine comprising a ballast tamping unit and the tool being arranged rearwards of the tamping unit in the direction advancement of the machine.

6. In the apparatus of claim 1, the signal emitter being a digital time measuring device.

7. In the apparatus of claim 1, the indicator including a system of lamps for stepwise actuation by the signal emitter for visual indication of the received time signals.

8. In the apparatus of claim 7, the system of lamps being arranged for stepwise actuation of an increasing number of the lamps in response to an increasing value in the time signal.

9. In the apparatus of claim 8, a voltage regulator being interposed between the signal emitter and the system of lamps for changing the light intensity of the lamps in response to a changing value in the time signal.

10. In the apparatus of claim 8, the system of lamps consisting of groups of differently colored lights, the lamps in each of the groups being responsive to corresponding time signals.

11. In the apparatus of claim 1, the indicator being a digital indicator for indicating the time signals in numbers.

* * * * *